United States Patent [19]

Fang

[11] Patent Number: 5,886,040
[45] Date of Patent: *Mar. 23, 1999

[54] CREATINE PYRUVATE SALT WITH ENHANCED PALATABILITY

[75] Inventor: Sen-Maw Fang, North Salt Lake, Utah

[73] Assignee: AMT Labs, Inc., North Salt Lake, Utah

[*] Notice: This patent issued on a continued prosecution application filed under 37 CFR 1.53(d), and is subject to the twenty year patent term provisions of 35 U.S.C. 154(a)(2).

[21] Appl. No.: 877,612

[22] Filed: Jun. 17, 1997

[51] Int. Cl.$^6$ .......................... A61K 31/19; A61K 31/155
[52] U.S. Cl. ............................................ 514/557; 514/634
[58] Field of Search ...................................... 514/557, 634

[56] References Cited

U.S. PATENT DOCUMENTS

| | | | |
|---|---|---|---|
| 4,158,057 | 6/1979 | Stanko | 514/251 |
| 4,351,835 | 9/1982 | Stanko | 514/251 |
| 4,415,576 | 11/1983 | Stanko | 514/251 |
| 4,548,937 | 10/1985 | Stanko | 514/251 |
| 4,645,764 | 2/1987 | Stanko | 514/251 |
| 4,812,479 | 3/1989 | Stanko | 514/557 |
| 4,874,790 | 10/1989 | Stanko | 514/557 |
| 5,047,427 | 9/1991 | Williamson | 514/557 |
| 5,134,162 | 7/1992 | Stanko | 514/557 |
| 5,253,697 | 10/1993 | LaJoyce et al. | 164/97 |
| 5,283,260 | 2/1994 | Miller et al. | 514/563 |
| 5,294,641 | 3/1994 | Stanko | 514/540 |
| 5,395,822 | 3/1995 | Izumi et al. | 514/3 |
| 5,397,786 | 3/1995 | Simone | 514/300 |
| 5,480,909 | 1/1996 | Stanko | 514/557 |
| 5,508,308 | 4/1996 | Miller et al. | 514/563 |
| 5,576,316 | 11/1996 | Cohn | 514/218 |
| 5,602,183 | 2/1997 | Martin et al. | 514/724 |
| 5,612,374 | 3/1997 | Stanko | 514/557 |
| 5,614,561 | 3/1997 | Martin | 514/724 |

OTHER PUBLICATIONS

Cannan, Shore, *CXV. The Creatine–Creatinine Equilibrium. The Apparent Dissociation Constants of Creatine and Creatinine,* 22 Biochem. J. 924, 1928.

Hultman E. et al., *Energy metabolism and fatigue.* 73–92.

Cortez et al., Effects of pyruvate and dihydroxyacetone consumption on the growth and metabolic state of obese Zucker rats, 53 American Journal of Clinical Nutrition 847–853, 1991.

Greenhaff et al., Influence of oral creatine supplementation of muscle torque during repeated bouts of maximal voluntary exercise in man, 84 Clinical Science 565–571, 1993.

Harris et al., Elevation of creatine in resting and exercised muscle of normal subjects by creatine supplementation, 83 Clin. Sci. 367–74, 1992.

Walker J.B. Creatine: Biosynthesis, regulation, and function, 50 Adv. Enzymology and Related Areas of Molecular Biology 177–242, 1979.

Stanko et al., Enhancement of arm exercise endurance capacity with dihydroxyacetone and pyruvate, 68 Journal of Applied Physiology 119–124, 1990.

Stanko et al., Enhanced leg–exercise endurance with a high–carbohydrate diet and dihydroxyacetone and pyruvate, 69 Journal of Applied Physiology 1651–1656, 1990.

Stanko et al., Body composition and Energy Utilization and nitrogen metabolism with a 4.25–MJ/d low–energy diet supplement with pyruvate, 56 American Journal of Clinical Nutrition 630–635, 1992.

Stanko et al., Inhibition of lipid accumulation and enhancement of energy expenditure by the Addition of Pyruvate and Dihrdyoxyacetone consumption on the growth and metabolic State of Zucker Rats, 35 Metabolism 182–286, 1986.

Stanko et al., Inhibition of lipid accumulation and enhancement of energy expenditure by addition of pyruvate and dihydroxyacetone to a rat diet, 35 Metabolism 182–186, 1986.

*Primary Examiner*—Kevin E. Weddington
*Attorney, Agent, or Firm*—Thorpe, North & Western

[57] ABSTRACT

An organic salt formed between creatine and pyruvic acid and their attendant salts and analogs, is water soluble and possesses improved palatability. The creatine is in a chemical form which increases its resistance to aqueous acid hydrolysis. The creatine cation provides the additional energy which the demands of a pyruvate induced metabolic state require. The result is a salt, which, when ingested results in increased energy and an enhanced metabolic rate.

8 Claims, No Drawings

CREATINE PYRUVATE SALT WITH ENHANCED PALATABILITY

This invention relates to the formation of a creatine pyruvate salt that is soluble in water and presents unique and useful synergistic attributes because of the ionic combination and provides a significantly improved taste over creatine salts of record.

BACKGROUND OF THE INVENTION AND DESCRIPTION OF PRIOR ART

Creatine, also known as N-(Aminoiminomethyl)-N-methylglycine, methylglycocyamine or (α-methyl-guanido) acetic acid is listed in the MERCK INDEX, an accepted chemical encyclopedia and may be represented by the following depiction:

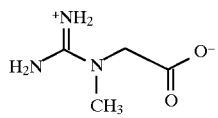

The Merck Index Twelfth Edition, No. 2637. Perhaps because of the positioning of the $NH_2$ gamma to the carboxylic acid, creatine is labile to acid hydrolysis. Regardless, however, of any purported rational, creatine is susceptible to cyclization under acid conditions to form creatinine which may be represented by the following formula:

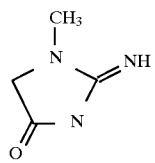

Indeed, dependent on the pH, an equilibrium is reached where creatine and creatinine exist at a certain ratio. Cannan, Shore, *Biochem. J.* 22, 924 (1928). Creatinine is, as well, one by-product of normal metabolic use of creatine and has been used as a diagnostic marker of such use. Moreover, the exposure of creatine to the acidic environment of the stomach would be expected to cause the irreversible formation of creatinine precluding further biological use of ingested creatine. Furthermore, the ingestion of creatine has been associated with marked stomach and gastric upset. Although the ingestion of creatine and gastric upset are perhaps only linked by empirical observation, the acid lability of creatine and subsequent formation of creatinine provide potential reasons.

Muscle contraction and relaxation are fueled by the free energy liberated by the dephosphorylation of adenosinetriphosphate (ATP). The ATP stored within cells is rapidly depleted during even normal activity. For normal tissue function to continue, ATP must be rapidly resynthesized from its breakdown products, one of which is adenosine diphosphate (ADP). During maximal exercise of a short duration this resynthesis is accomplished almost exclusively by the anaerobic degradation of phosphocreatine (PCr) and glycogen. Hultman E. et al.; Energy metabolism and fatigue. In: Taylor A, Gollnick P, Green H, et al., eds. *Biochemistry of exercise* VII. Champaign, Ill.: Human Kinetic Publishers, 1990: vol. 21, 73–92. Greenhaff et al. proposed that the observed decline in force production during intense contraction may be related to the availability of muscle PCr stores. Greenhaff P. L., Casey A., Short A. H., Harris R., Soderlund K., Hultman E.; Influence of oral creatine supplementation of muscle torque during repeated bouts of maximal voluntary exercise in man; *Clinical Science* (1993) 84, 565–571. The depletion of these PCr stores limits the re-phosphorylation of ADP, thereby limiting the ATP available for energy production. Greenhaff et al. further proposed that any mechanism capable of increasing the intramuscular total creatine store might arrest PCr depletion during intense muscular contraction and offset or even prevent the decline in the rate of ADP re-phosphorylation during exercise. Grennhaff et al. did not present any solution whereby the effective amount of creatine within the muscle cells could be increased. Indeed, Greenhaff et al. relied upon work previously published by Harris et al. where it was demonstrated that the creatine content of skeletal muscles may be increased, however by only 20%–50%, through standard oral pathways. Importantly, in order to achieve this increase in the creatine content of muscle cells the subjects of the study were required to ingest 20 grams of creatine monohydrate, much of which was washed out through the urine prior to use. Harris R C, Soderlund K, Hultman E.; Elevation of creatine in resting and exercised muscle of normal subjects by creatine supplementation., *Clin. Sci.*, 1992; 83: 367–74.

Creatine can be found biologically in many forms and in diverse portions of the body. Walker report creatine to exist mainly in the nerves and muscle. Walker J. B.; Creatine: Biosynthesis, regulation, and function; *Adv. Enzymology and Related Areas of Molecular Biology* (1979) 50: 177–242. Creatine has a normal turnover rate of ~2 grams per day. The biochemical process which uses creatine for the regeneration of ATP from ADP irreversibly transforms creatine to creatinine which is eliminated through the urine. Because creatine is irreversibly used, the body must either produce creatine biochemically or secure an outside source for the needed creatine.

Biochemically creatine is synthesized in the human liver and pancreas whereas creatine is synthesized exclusively in the liver by members of the poultry family. The human liver and pancreas use the amino acids glycine, serine, arginine and methionine to synthesize creatine. However, where sufficient creatine is made bioavailable through ingestion such biosynthesis would seem to be minimized. Although animal muscle contains approximately 0.5% creatine by weight, most of this is degraded by cooking thereby precluding cooked meat from the potential list of external sources of ingestible creatine. Moreover, neither plant nor vegetable matter provides a significant source of creatine.

Creatine has been utilized as a component of compositions taught in several recent U.S. patents. U.S. Pat. No. 5,397,786 entitled REHYDRATION DRINK discloses and claims a rehydration drink for the treatment and prevention of the loss of essential electrolytes because of fluid loss. This patent teaches that creatine, B vitamins, pantothenic acid and choline are energy enhancers. Additionally, this invention provides for the addition of numerous salts such as $MgCO_3$, $CaCO_3$ and magnesium aspartate as a supplement which contains essential nutrients. However the use of ionic salts such as $MgCO_3$ is less effective than desired because most of the ingested element is lost in the acidic environment of the stomach.

U.S. Pat. No. 5,576,316 entitled METHOD FOR INHIBITING TUMOR GROWTH RATE USING CREATINE OR CREATINE ANALOGS issued Nov. 19, 1996. This patent teaches the use of creatine and creatine analogs for the treatment of tumors. Specifically it is alleged that the administration of creatine in the form of a salt can reduce a tumor's growth rate. This patent also teaches that significant portions of orally administered creatine are lost through the urine without having been used by the host.

Pyruvic acid in various organic and inorganic derivatives, is found in diverse tissue systems and regions of the body. Pyruvic acid, a simple keto-acid may be represented by the following formula.

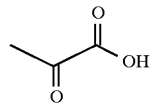

It is liquid at ambient temperature and somewhat similar to acetic acid in taste and odor. Pyruvic acid becomes anionic when the pH becomes more basic than the pKa of the carboxylic acid moiety of the molecule. Following the expected ionization of the acidic portion pyruvic acid yields the cation $H^+$ and the anion pyruvate. Importantly, the use of the suffix "ate" connotes an ionic or salt form of an organic molecule. Accordingly, pyruvic acid could be transformed into the sodium salt of pyruvic acid through the reaction of pyruvic acid with sodium hydroxide to form sodium pyruvate, wherein the ate ending denotes the formation of a salt from pyruvic acid. To one skilled in the art it will be apparent that an inorganic salt is the salt formed from the reaction of inorganic acids (HCl, $H_2SO_4$, HI, etc) and inorganic bases (NaOH, $NH_4Cl$, etc). Additionally, an inorganic salt would also include any salt which contains an inorganic cation or anion as exemplified infra.

U.S. Pat. No. 5,612,374 titled INHIBITING GROWTH OF MAMMARY ADENOCARCINOMA issued to Ronald Stanko is directed to the administration of pyruvate salts to inhibit the growth of mammary adenocarcinoma. The patent teaches the use of sodium and calcium salts and organic esters of pyruvic acid.

U.S. Pat. No. 5,480,909 titled METHOD FOR INHIBITING GENERATION OF FREE-RADICALS issued to Ronald Stanko discloses the use of pyruvate as a free radical scavenger. According to this invention, a patient who is experiencing, or who is expected to experience, bodily stress which might result in free radical generation receives appropriate dosages of pyruvate before, during and following each free radical generating incident. This patent discloses several forms of pyruvate, namely calcium pyruvate, pyruvate esters and other organic pyruvate analogs.

U.S. Pat. No. 5,294,641 entitled METHOD FOR TREATING A MEDICAL PATIENT FOR CARDIAC TRAUMA issued to Ronald Stanko discloses a method which uses pyruvate for the treatment of the adverse effects of ischemia. This is accomplished by introducing a therapeutic quantity of pyruvate into the blood stream of the patient prior to the surgical procedure to increase the patient's cardiac output. One alternative is presented wherein the patient may take effective oral dosages of pyruvate prior to and during periods of potential risk.

U.S. Pat. No. 5,614,561 titled ANTIHISTAMINE WOUND HEALING COMPOSITIONS AND METHODS FOR PREPARING AND USING SAME, to Alain Martin discloses a composition which contains pyruvate, an antioxidant and a mixture of saturated and unsaturated fatty acids, as a wound healing composition. The combination of a topical antihistamine agent and the wound healing composition is said to be useful for treating itching associated with skin irritations and further increase the resuscitation rate of injured mammalian cells.

U.S. Pat. No. 5,602,183 entitled DERMATOLOGICAL WOUND HEALING COMPOSITIONS AND METHODS FOR PREPARING AND USING SAME to Alain Martin discloses a wound healing composition which is composed of pyruvate, an antioxidant and a mixture of saturated and unsaturated fatty acids. This invention pertains to therapeutic dermatological wound healing compositions useful to minimize and treat diaper dermatitis.

U.S. Pat. No. 4,351,835 entitled METHOD FOR PREVENTING BODY FAT DEPOSITION IN MAMMALS issued to Ronald T. Stanko discloses a method for reducing the rate of liver triglyceride synthesis and body fat deposition in mammals by orally administering over a prolonged period a mixture of pyruvate and dihydroxyacetone.

U.S. Pat. No. 5,508,308 entitled USE OF PYRUVYLGLYCINE TO TREAT ISCHEMIA/REPERFUSION INJURY FOLLOWING MYOCARDIAL INFARCTION issued to Robert H. Miller discloses that pyruvate, as pyruvylglycine, provides protection to mammalian heart muscle which has been deprived of a blood supply and, therefore, oxygen; which can occur during a heart attack. Pyruvylglycine is not the salt of glycine and pyruvic acid but rather is a single organic molecule which contains sections which correspondingly resemble a pyruvic acid molecule and a glycine molecule.

U.S. Pat. No. 5,134,162 titled METHOD FOR LOWERING HIGH BLOOD CHOLESTEROL LEVELS IN HYPERLIPIDEMIC ANIMALS AND CONFECTIONS AS THE INGESTION MEDIUM issued to Ronald Stanko discloses a method whereby the blood cholesterol level of a hyperlipidemic patient is lowered through the ingestion of pyruvate.

U.S. Pat. No. 4,874,790 titled METHOD FOR IMPROVING THE GLUCOSE METABOLISM OF AN ANIMAL HAVING DIABETIC TENDENCIES issued to Ronald Stanko discloses a method for treating animals having diabetic tendencies to improve the glucose metabolism of the animal by oral administration of an effective amount of pyruvate and dihydroxyacetone.

U.S. Pat. No. 4,812,479 titled METHOD FOR PREVENTING BODY FAT DEPOSITION IN MAMMALS issued to Ronald T. Stanko is directed to a method for reducing the weight gain in an animal by administering over a prolonged period a therapeutically effective amount of dihydroxyacetone. This method also includes the administration of a mixture of dihydroxyacetone and pyruvate to increase the glycogen store in the liver.

U.S. Pat. No. 4,645,764 titled METHOD FOR PREVENTING BODY FAT DEPOSITION IN ANIMALS issued to Ronald Stanko is directed to a method for reducing body fat deposition in non-mammals. Specifically this invention teaches a method for controlling weight gain in chickens by means of coadministering pyruvate and dihydroxyacetone, preferably along with riboflavin.

U.S. Pat. No. 4,548,937 titled METHOD FOR PREVENTING BODY FAT DEPOSITION IN MAMMALS issued to Ronald Stanko discloses a method for reducing the weight gain or controlling the weight gain in mammals through the administration over a prolonged period of effective amounts of pyruvate.

U.S. Pat. No. 4,415,576 titled METHOD FOR PREVENTING BODY FAT DEPOSITION IN MAMMALS issued to Ronald Stanko is directed to a method for reducing the rate of liver triglyceride synthesis and body fat deposition in mammals through the administration of an effective amount of a mixture of pyruvate and dihydroxyacetone.

U.S. Pat. No. 4,158,057 titled PREVENTION OF THE ACCUMULATION OF FATTY DEPOSITS IN THE LIVER issued to Ronald Stanko discloses a method for preventing the accumulation of fatty deposits in mammalian livers secondary to the ingestion of alcohol. The method herein disclosed consists of administering a suitable dosage of a mixture of dihydroxyacetone and pyruvate. The invention disclosed is specifically drawn to the prevention of fat deposition in livers of mammals where alcohol consumption has or will occur. Pyruvate is defined to mean pyruvic acid and not a salt thereof.

U.S. Pat. No. 5,283,260 titled METHOD FOR REDUCING INSULIN RESISTANCE IN MAMMALS issued to Robert H. Miller is directed to a method for the administration of pyruvate salts, pyruvyl-amino acid compounds and pyruvate precursors to cause a reduction in insulin resistance in mammals. This patent teaches the use of simple metal salts of pyruvic acid e.g., Na, K and Ca pyruvates and chemically modified pyruvate analogues such as pyruvyl-glycine.

U.S. Pat. No. 5,256,697 titled METHOD OF ADMINISTERING PYRUVATE AND METHODS OF SYNTHESIZING PYRUVATE PRECURSORS issued to Robert Miller is drawn to a method of administering pyruvate precursors, pyruvate salts and pyruvyl-amino acid compounds. This patent teaches the use of simple metal salts of pyruvic acid e.g., Na, K and Ca pyruvates and chemically modified pyruvate analogues such as pyruvyl-glycine.

U.S. Pat. No. 5,047,427 titled TREATMENT FOR SECONDARY DIABETES EFFECTS issued to Joseph Williamson is directed to dietary supplements which are capable of preventing the secondary effects of diabetes in cells characterized by glucose uptake mechanisms which are not regulated by insulin. The disclosed invention is directed to a method to reduce the effects of diabetes through the administration of an effective amount of pyruvate salts. This patent teaches the use of simple metal salts of pyruvic acid e.g., Na, K and Ca pyruvates.

U.S. Pat. No. 5,395,822 titled USE OF PYRUVATE TO PREVENT NEURONAL DEGENERATION ASSOCIATED WITH ISCHEMIA issued to Yukitoshi Izumi discloses a method of using a metal salt of pyruvic acid to protect against neuronal degeneration do to ischemia or due to hypoxia, hypoglycemia which interfere with the energy metabolism of neurons. This patent teaches the use of simple metal salts of pyruvic acid e.g., Na, K and Ca pyruvates.

Although the administration of pyruvic acid or an inorganic salt thereof has allegedly contributed to numerous beneficial physiological results, all previous publications teach administration of inorganic salts of pyruvic acid alone or in admixture with other ingredients such as dihydroxyacetone. Most prior art seems to teach that it is the combined administration of dihydroxyacetone and the inorganic salt of pyruvic acid that causes the desired result. Additional scientific publication have demonstrated that the administration of pyruvate and dihydroxyacetone increases arm muscle glucose extraction both before and during exercise thereby enhancing submaximal arm endurance capacity. Stanko et al., Enhancement of arm exercise endurance capacity with dihydroxyacetone and pyruvate.; *Journal of Applied Physiology* 68: 119–124, 1990. Further study by Stanko et al. revealed a 63% improvement in leg glucose concentration following 30 minutes of exercise. Stanko et al, Enhanced leg-exercise endurance with a high-carbohydrate diet and dihydroxyacetone and pvruvate.; *Journal of Applied Physiology* 69: 1651–1656, 1990. Pyruvate has also been shown to reduce fat accumulation by 32% in rats. Stanko et al., Inhibition of lipid accumulation and enhancement of energy expenditure by addition of pyruvate and dihydroxyacetone to a rat diet.; *Metabolism* 35: 182–186, 1986. Moreover pyruvate and dihydroxyacetone has been shown to have a beneficial impact on weight as altered by fat loss. Obese female subjects which were fed pyruvic acid as a dietary supplement lost 37% more weight and 48% more fat than the control group. Stanko et al., Body composition and Energy Utilization and nitrogen metabolism with a 4.25-MJ/d low-energy diet supplement with pyruvate. *American Journal of Clinical Nutrition;* 56: 630–635, 1992. Additional studies on animals have shown that the addition of pyruvate and dihydroxyacetone to the diet leads to increased rates of heat production and energy expenditure. Stanko eg al., Inhibition of lipid accumulation and enhancement of energy expenditure by the Addition of Pyruvate and Dihydroxyacetone consumption on the growth and metabolic State of Zucker Rats. *American Journal of Clinical Nutrition;* 53: 847–853, 1991. It is noteworthy that all previous publications employ the simple metal salt of pyruvic acid. Furthermore the pyruvate salt is usually mixed with another substance such as dihydroxy acetone.

From the above it is apparent that each creatine and pyruvic acid and their attendant salts and analogs have beneficial physiological properties. However, one drawback associated with their administration is that of palatability. Neither creatine nor pyruvic acid, or their simple salts, have a pleasant taste. Pyruvic acid is a liquid that, as noted above, is somewhat similar to acetic acid in odor and taste. Simple salts of pyruvic acid, are solids, but somewhat resemble the odor and flavor of the acid. In addition, when administered as simple salts, such as sodium, potassium, calcium, etc., they include a metal cation that may not be beneficial.

In view of the foregoing, it will be appreciated that the oral administration of a single composition incorporating both pyruvate and creatine as a palatable organic salt which retains, or even enhances, the bioeffectiveness of each, would be a significant advancement in the art.

SUMMARY OF THE INVENTION

It is an object of the present invention to provide an organic salt which is formed between an energy enhancing cationic portion, represented by creatine, and a metabolic rate enhancing anion portion, represented by pyruvate, where said salt can be administered orally to a mammal and have a bioavailability that is equal to or greater than creatine or pyruvate administered separately or as a mixture.

A further object of the present invention is to provide a bioavailable creatine/pyruvate salt which is administered orally and which salt has improved palatability.

An additional object of the invention is to synergistically combine into a non metal containing ionic compound an energy enhancing cation, represented by creatine, and an energy enhancing anion, represented by pyruvate.

These and other objects may be accomplished by means of an organic salt formed of creatine and pyruvic acid and their attendant salts and analogs. As used herein the term "pyruvate" will connote a salt of pyruvic acid. This salt can be of any type or form such as the salt of pyruvic acid and an inorganic base or the salt of pyruvic acid and an organic base such as an amine. Pyruvate analogue will connote a substance which is made from chemical manipulation of pyruvic acid such as the formation of the methyl pyruvate ester from a reaction of methyl alcohol and pyruvic acid. Similarly, a creatine analogue will connote a substance which is made from chemical manipulation of creatine such as the formation of creatine acetamide from a reaction of creatine with acetic acid.

Creatine pyruvate monohydrate may be represented by the empirical formula: $C_3H_3O_3^-.C_4H_{10}O_2N_3^+.H_2O$. The actual structural formula is now known for a certainty. However, it is known that the reaction between creatine and pyruvate is exothermic and that an organic salt is formed. It is also known that the salt formed is of relatively pure quality in that the product formed is a crystalline solid that has a definite decomposition point of 112°–114° C. Such a product is significantly different from its reactants. Creatine monohydrate is a solid that is sparingly soluble in water and that equilibrates in water to form creatine and creatinine. Pyruvic acid is a liquid that polymerizes and decomposes on standing unless stored in an airtight container.

While current data would indicate that a 1:1 mole ratio of creatine to pyruvate provides the optimal results in energy production and metabolic rate increase it is anticipated that the ratio of creatine to pyruvate may vary between about 0.5:1 to 2:1.

EXAMPLE 1

One mole of creatine monohydrate with a molecular weight of 149.15 g/mole is mixed with one mole of pyruvic acid having a molecular weight of 88.06 g/mole. To this mixture is added 20 gms of a 1:1 v/v mixture of isopropyl alcohol and water. The powder and liquid are stirred together while being held at or below 60° C. by a cooling bath at that temperature until the mixture solidifies. The resultant powder is dried to yield crystalline creatine pyruvate monohydrate. This product has a molecular weight of 237.21 and decomposes at 112°–114° C.

The resultant product is a stable off-white powder of the formula: $C_3H_{3O3}^-.C_4H_{10}O_2N_3^+.H_2O$ having a faint but distinct smell of pyruvic acid. Unlike creatine monohydrate, the resultant creatine pyruvate monohydrate compound is quite water soluble. Additionally it should be noted that the reaction for the formation of creatine pyruvate is exothermic as evidenced by the necessity for a cooling bath during formation. The reason why this reaction is exothermic is not clear. However, because the formation of most simple salts is ambi-thermic, non-heat producing, this exotherimicity implies that the resultant creatine pyruvate is not a simple salt.

EXAMPLE 2

A panel of ten people were given samples of creatine monohydrate and the creatine pyruvate monohydrate as formed in Example 1 to taste. The creatine pyruvate monohydrate had a pleasant sour taste and was preferred, in all instances, to creatine monohydrate. However, if desired, a sweetener, such as sucrose, fructose, glucose, aspartame and the like can be used to further enhance the taste and offset the slightly sour taste of the creatine pyruvate monohydrate.

EXAMPLE 3

The resultant creatine pyruvate monohydrate solid from Example 1, in dosages of from about 5 to 20 gms, can be mixed with 8 oz. water or juice and taken as an exercise supplement. This supplement can be taken such that between 20 gms to 50 gms of the creating pyruvate salt is ingested each 24 hour period.

The ingestion of creatine pyruvate monohydrate is well tolerated and has not been linked with known difficulties. Any unused quantities are believe to be excreted.

The two moieties of the organic salt namely creatine and pyruvate each provide unique characteristics regarding energy enhancement, carbohydrate metabolism, glycogen metabolism and fat deposition. Importantly, the combination of creatine and pyruvate into the same salt compound produces characteristics that are not to be found in either product alone. It has already been pointed out that the organic salt avoids the use of metal cations, enhances the solubility of the creatine portion and improves palatability. This makes it much easier to formulate and administer a single compound as a salt while retaining the beneficial physiological properties of both creatine and pyruvic acid.

In summary, it is to be noted that creatine is of limited water solubility and is irreversibly altered to creatinine by aqueous acid. On the other hand, pyruvic acid, is a liquid that is absorbed readily through the stomach wall without significant metabolism. Pyruvic acid and its inorganic salts, as pyruvates, increase the metabolic rate of mammals thereby requiring more fuel expenditure but are not pleasant to the taste. The creatine pyruvate monohydrate salt of the present invention greatly increases solubility of the creatine portion of the salt, improves palatability, and enables the optimal biofunctionality of both creating and pyruvate in enhancing energy and metabolic rates. In other words, the creatine pyruvate salt of the present invention is water soluble; the creatine is in a chemical form that increases its resistance to aqueous acid hydrolysis; and, the creatine cation provides the additional energy that the demands of a pyruvate induced metabolic state require.

I claim:

1. A soluble organic salt of a creatine member and a pyruvate member having a creatine member to pyruvate member molar ratio of between 0.5:1 to 2:1.

2. A salt according to claim 1 wherein the creatine member is selected from the group consisting of creatine, creatine esters, creatine amides, creatine imides and mixtures thereof.

3. A salt according to claim 2 wherein the pyruvate member is selected from the group consisting of pyruvic acid, pyruvic acid salts and mixtures thereof.

4. A salt according to claim 3 wherein the molar ratio of the creatine member and the pyruvate member is 1:1.

5. A salt according to claim 4 wherein the creatine member is creatine.

6. A salt according to claim 5 wherein the pyruvate member is pyruvic acid.

7. A salt according to claim 6 wherein creatine is the cation and pyruvate is the anion.

8. A salt according to claim 7 having the formula: $C_3H_3O_3^-.C_4H_{10}O_2N_3^+.H_2O$.

* * * * *